United States Patent
Reinhardt et al.

(10) Patent No.: US 8,980,127 B2
(45) Date of Patent: Mar. 17, 2015

(54) METHOD FOR PRODUCING 3,7-DIAZA-BICYCLO[3.3.1]NONANE-METAL COMPLEX SOLUTIONS

(75) Inventors: Gerd Reinhardt, Kelkheim (DE); Miriam Ladwig, Dietzenbach (DE)

(73) Assignee: Clariant International Ltd., Muttenz (CH)

( * ) Notice: Subject to any disclaimer, the term of this patent is extended or adjusted under 35 U.S.C. 154(b) by 145 days.

(21) Appl. No.: 13/575,791

(22) PCT Filed: Jan. 28, 2011

(86) PCT No.: PCT/EP2011/000403
§ 371 (c)(1),
(2), (4) Date: Oct. 10, 2012

(87) PCT Pub. No.: WO2011/095307
PCT Pub. Date: Aug. 11, 2011

(65) Prior Publication Data
US 2013/0032754 A1 Feb. 7, 2013

(30) Foreign Application Priority Data
Feb. 6, 2010 (DE) .......... 10 2010 007 058

(51) Int. Cl.
C09K 3/00 (2006.01)
C07D 471/08 (2006.01)
C07F 13/00 (2006.01)
C07F 15/02 (2006.01)

(52) U.S. Cl.
CPC ............ C07D 471/08 (2013.01); C07F 13/005 (2013.01); C07F 15/025 (2013.01)
USPC .................................................. 252/182.12

(58) Field of Classification Search
USPC .................................................. 252/182.12
See application file for complete search history.

(56) References Cited

U.S. PATENT DOCUMENTS

| | | | |
|---|---|---|---|
| 6,653,270 B2 * | 11/2003 | LaBeque ................. | 510/311 |
| 6,818,149 B2 | 11/2004 | Boerzel et al. | |
| 7,205,267 B2 * | 4/2007 | Reinhardt et al. ........... | 510/311 |
| 7,501,389 B2 * | 3/2009 | Hage et al. .................. | 510/376 |
| 8,536,334 B2 * | 9/2013 | Sajitz et al. ................ | 546/10 |
| 2002/0149000 A1 * | 10/2002 | Boerzel et al. ............. | 252/188.1 |
| 2003/0230736 A1 * | 12/2003 | Hage et al. ................. | 252/186.39 |
| 2004/0014625 A1 * | 1/2004 | Comba et al. ............... | 510/311 |
| 2005/0209120 A1 * | 9/2005 | Reinhardt et al. .......... | 510/312 |
| 2008/0035885 A1 * | 2/2008 | Hage et al. ................. | 252/186.24 |
| 2008/0193378 A1 | 8/2008 | Comba et al. | |
| 2009/0234124 A1 * | 9/2009 | Wessling et al. ........... | 546/123 |
| 2011/0003984 A1 * | 1/2011 | Comba et al. .............. | 540/541 |

FOREIGN PATENT DOCUMENTS

| | | | |
|---|---|---|---|
| DE | 102004062568 B3 | 2/2006 | |
| DE | 60120781 T2 | 1/2007 | |
| DE | 102008064009 A1 | 6/2010 | |
| EP | 1700907 * | 9/2006 | |
| WO | 0116271 A1 | 3/2001 | |
| WO | 0248301 A1 | 6/2002 | |
| WO | 03104234 A1 | 12/2003 | |
| WO | WO 2005042532 A1 * | 5/2005 | ........... C07D 471/08 |
| WO | 2006072336 A2 | 7/2006 | |
| WO | 2006133869 A1 | 12/2006 | |
| WO | 2008003652 A1 | 1/2008 | |
| WO | 2009010129 A1 | 1/2009 | |
| WO | 2010069524 A1 | 6/2010 | |
| WO | WO2010069524 * | 6/2010 | |

* cited by examiner

*Primary Examiner* — Nicole M Buie-Hatcher
*Assistant Examiner* — M. Reza Asdjodi
(74) *Attorney, Agent, or Firm* — Michael W. Ferrell

(57) ABSTRACT

The invention relates to a method for producing homogeneous solutions of metal complexes of general formula (2): $[M_aL_xX_n]Y_m$, where M is a metal from the group comprising Mn(II), Mn(III), Mn(IV), Fe(III), Fe(III) or Fe(IV), X is a coordinated compound selected from mono- bi- or tri-charged anions or neutral molecules which are able to coordinate with a metal mono- bi- or tri-dentate, Y is a non-coordinated counter-ion which ensures charge equalization of the complex, L is a ligand of general formula (1) or the protonized or de-protonized form thereof, and a, x, n, m, R, $R^1$, $R^2$, $R^3$ and z are as specified in claim 1, in diols or polyols, the monoethers or mixtures of said substances. Said method is characterized in that a ligand of the formula (1) is reacted with an iron or manganese salt in a heterogeneous reaction in the diol or polyol, the monoethers or mixtures of these substances.

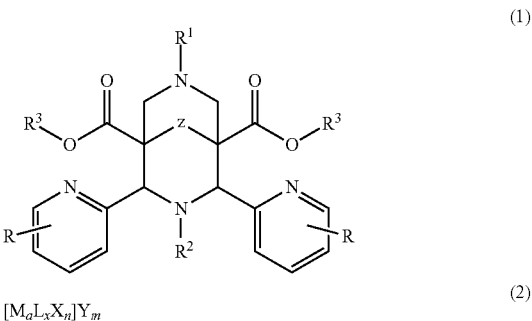

20 Claims, No Drawings

METHOD FOR PRODUCING 3,7-DIAZA-BICYCLO[3.3.1]NONANE-METAL COMPLEX SOLUTIONS

The invention relates to a process for preparing 3,7-diazabicyclo-[3.3.1]nonane-iron or -manganese complex solutions in aprotic organic solvents, especially in propylene glycols, by in situ complexation of a ligand compound with a metal salt.

3,7-Diazabicyclo[3.3.1]nonane compounds are compounds of interest for various applications. Among other things, transition metal complexes containing a ligand of the formula (1) are very effective catalysts which, in combination with atmospheric oxygen, can be used for bleaching of oily stains in washing and cleaning compositions. It is possible here to dispense with the use of the otherwise customary hydrogen peroxides or inorganic per salts. Examples thereof are described in WO 03/104234.

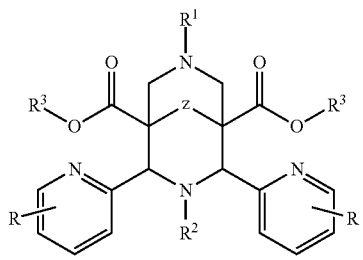

(1)

Due to their mechanism of action with oxygen, a further field of use has opened up for this substance class in recent times. For instance, WO 2008/003652 describes the use of such transition metal complexes as catalysts for the drying of alkyd-based paints and coatings. They serve here as an environmentally friendly alternative to cobalt-containing fatty acid derivatives, which are suspected of causing cancer. For use in paints and coatings, the complexes are usually used in dissolved form, for example as a 1% by weight solution in propylene glycol, as described, for example, in the reference available at the web address "www.rahucat.com/pdfs/Borchi_OXY_Coat_ECS_Congress.pdf"

Ligands of the formula (1) and metal complexes thereof have been described in detail in the literature. The ligand synthesis is described, for example, in WO 2006/133869, while WO 02/48301, Inorg. Chimica Acta, 337 (2002) 407-419 and Eur. J. Org. Chem. (2008) 1019-1030 describe complexation reactions. These involve dissolving both the ligand and the metal salt separately in different organic solvents and then conducting the complex formation in homogeneous solution. Since the metal complexes also have good solubility in the solvent mixture, a further solvent has to be used for isolation of the complexes, in order to be able to isolate the product in crystalline form. Solutions of the complexes in propylene glycol thus isolated can then be prepared by dissolving the powders in propylene glycol. For this purpose, due to the sparing solubility of the complexes in propylene glycol, however, long reaction times are necessary.

This process corresponding to the prior art is uneconomic since, firstly, various solvents are used, which subsequently have to be worked up, and, secondly, the complex first has to be isolated and dried and then dissolved again. There was therefore a need for a process performable on the industrial scale for preparation of solutions of such complexes, which can dispense with isolation and drying of the complex.

It has now been found that, surprisingly, solutions of iron and manganese complexes of the formula (2) can be prepared in situ in di- or polyol, monoethers thereof or mixtures of these substances, and especially in propylene glycol, even though ligands of the formula (1) are virtually insoluble in these solvents. Moreover, it could not be clear to the person skilled in the art that, under the selected conditions, it is possible to form a complex of the formula (2) in which the carbonyl group is present as the dihydroxy ketal (hydrate), since operation is effected in the presence of solvent which can likewise enter into ketalization reactions under acidic reaction conditions.

The present invention therefore provides a process for preparing homogeneous solutions comprising one or more metal complexes of the formula (2)

$$[M_a L_x X_n] Y_m \quad (2)$$

where

M is a metal from the group of Mn(II), Mn(III), Mn(IV), Fe(II), Fe(III) and Fe(IV), X is a coordinating compound selected from singly, doubly and triply charged anions or uncharged molecules capable of mono-, bi- or tridentate coordination to a metal, preferably $OH^-$, $NO_3^-$, $NO_3^-$, $S^{2-}$, $R^aS^-$, $PO_4^{3-}$, $H_2O$, $CO_3^{2-}$, $R^bOH$, $Cl^-$, $Br^-$, $CN^-$, $ClO_4^-$, $R^aCOO^-$ and $SO_4^{2-}$, where $R^a$ is H or $C_1$-$C_4$ alkyl and $R^b$ is $C_1$-$C_4$ alkyl, more preferably $Cl^-$ or $SO_4^{2-}$ and especially preferably $Cl^-$, Y is a noncoordinating counterion which ensures the charge balance of the complex, preferably of $R^cSO_4^-$, $SO_4^{2-}$, $NO_3^-$, $Cl^-$, $Br^-$, $I^-$, $ClO_4^-$, $BF_4^-$, $PF_6^-$ and $R^cSO_3^-$, where $R^c$ is H or $C_1$-$C_4$ alkyl, more preferably $Cl^-$ or $SO_4^{2-}$ and especially preferably $Cl^-$, a is a number from 1 to 2,
x is a number from 1 to 2,
n is a number from 0 to 4,
m is a number from 0 to 8, and
L is a ligand of the formula (1) or the protonated or deprotonated form thereof

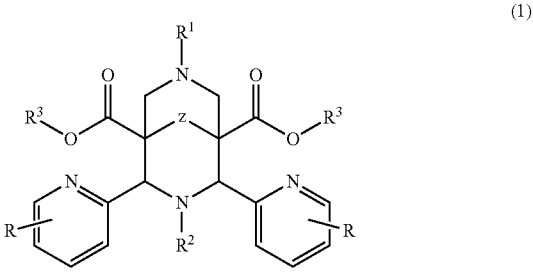

(1)

where

R is hydrogen, hydroxyl or $C_1$-$C_4$ alkyl;
$R^1$ is $C_1$-$C_4$ alkyl, $C_6$-$C_{10}$ aryl, pyridinyl-$C_1$-$C_4$-alkyl or $(CH_2)_k N(C_1$-$C_4$-alkyl)$_2$;
$R^2$ is $C_1$-$C_{20}$ alkyl, $C_6$-$C_{10}$ aryl or pyridinyl-$C_1$-$C_4$-alkyl;
$R^3$ is $C_1$-$C_4$ alkyl;
z is C=O or C(OH)$_2$ and
k is a number from 1 to 6, in di- or polyols, monoethers thereof or mixtures of these substances, which comprises reacting one or more ligands of the formula (1) with an iron or manganese salt in heterogeneous reaction in the di- or polyol, the monoethers or mixtures of these substances.

Particular preference is given to using the process according to the invention to prepare solutions comprising one or more complexes of the formula [FeLCl]Cl, [FeL(SO₄)], [MnLCl]Cl or [MnL(SO₄)] are prepared, where L is selected from the group consisting of
dimethyl 2,4-di(2-pyridyl)-3-methyl-7-(pyridin-2-ylmethyl)-3,7-diazabicyclo-[3.3.1]nonan-9-one-1,5-dicarboxylate (N2Py3o),
dimethyl 2,4-di(2-pyridyl)-3-(pyridin-2-ylmethyl)-7-methyl-3,7-diazabicyclo-[3.3.1]nonan-9-one-1,5-dicarboxylate (N2Py3u),
diethyl 2,4-di(2-pyridyl)-3-methyl-7-(pyridin-2-ylmethyl)-3,7-diazabicyclo-[3.3.1]nonan-9-one-1,5-dicarboxylate,
dimethyl 2,4-di(2-pyridyl)-3,7-bis(pyridin-2-ylmethyl)-3,7-diazabicyclo[3.3.1]-nonan-9-one-1,5-dicarboxylate (N2Py4),
dimethyl 2,4-di(2-pyridyl)-3,7-dimethyl-3,7-diazabicyclo[3.3.1]nonan-9-one-1,5-dicarboxylate (N2Py2),
diethyl 2,4-di(2-pyridyl)-3,7-dimethyl-3,7-diazabicyclo[3.3.1]nonan-9-one-1,5-dicarboxylate,
dimethyl 2,4-di(2-pyridyl)-3-methyl-7-(N,N'-dimethylethylamine)-3,7-diazabicyclo[3.3.1]nonan-9-one-1,5-dicarboxylate
and the corresponding dihydroxy ketals.

In an embodiment preferred in turn in this aspect of the invention, the process according to the invention is used to prepare solutions comprising one or more complexes of the formula [FeLC]Cl or [MnLCl]Cl and more preferably solutions comprising one or more complexes of the formula [FeLCl]Cl.

The di- or polyols used in the process according to the invention preferably have 2 to 6 carbon atoms and 2 to 4 OH groups, and the monoethers of these di- and polyols preferably contain alcohol units originating from monoalcohols having 1 to 4 carbon atoms and more preferably from saturated monoalcohols having 1 to 4 carbon atoms.

The process according to the invention is preferably conducted in di- or polyols or in mixtures thereof. The di- or polyols used are preferably ethylene glycol, 1,2-propylene glycol, 1,3-propylene glycol, glycerol or 1,4-butanediol, particular preference being given to 1,2-propylene glycol.

The solutions prepared by the process according to the invention contain preferably 0.01 to 30% by weight, more preferably 0.1 to 15% by weight and especially preferably 0.5 to 8% by weight of complex of the formula (2).

A further characterizing feature of the process according to the invention is that the complexation reaction takes place within the temperature range from preferably 5 to 80° C., more preferably 10 to 70° C. and especially preferably 15 to 55° C.

The iron or manganese salt used in the process according to the invention is also referred to hereinafter as "metal salt" for short.

The molar ratio of ligand of the formula (1):metal salt is preferably from 0.90:1 to 1.10:1, more preferably from 0.95:1 to 1.05:1.

The ligands can be prepared on the industrial scale according to the information in DE 601 20 781 or WO 2006/133869 as per the following reaction scheme:

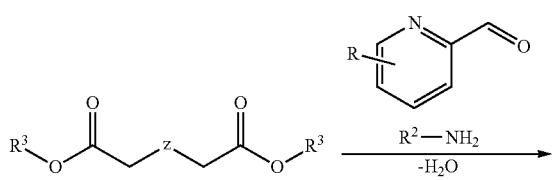

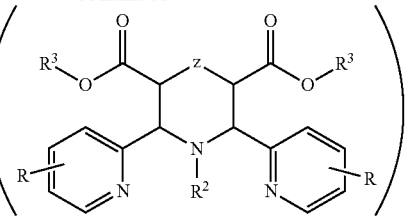

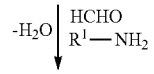

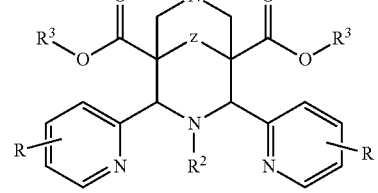

(1)

Proceeding from dicarboxylic diester, two Mannich condensation steps with elimination of water are conducted in a C₁-C₄ alcohol, for example ethanol, propanols or butanols. After removal of water has ended, the mixture is cooled and the product is filtered off and washed. According to the preparation, the ligands may be obtained in the form of crystals of greater or lesser size. For the complexation reaction, the ligands can then be used either in solvent-moist form or in dried form. Even though it is advantageous for the complexation reaction to use very small crystals in the heterogeneous complexation reaction, comminution is not absolutely necessary for the conversion to be successful.

In a further preferred embodiment of the process according to the invention, the ligands of the formula (1) are selected from the group consisting of dimethyl 2,4-di(2-pyridyl)-3-methyl-7-(pyridin-2-ylmethyl)-3,7-diazabicyclo[3.3.1]nonan-9-one-1,5-dicarboxylate (N2Py3o), dimethyl 2,4-di(2-pyridyl)-3,7-dimethyl-3,7-diazabicyclo[3.3.1]nonan-9-one-1,5-dicarboxylate (N2Py2) and the corresponding dihydroxy ketals.

The complexation reaction is performed by first introducing the one or more ligands of the formula (1) into di- or polyol, monoethers thereof or mixtures of these substances to prepare a suspension containing 0.5 to 60%, more preferably 1 to 60%, especially preferably 3 to 50% and exceptionally preferably 5 to 30% by weight of ligand. Subsequently, the metal salt is added in solid or dissolved form within the temperature range from 5 to 80° C., more preferably 10 to 70° C., especially preferably 15 to 55° C.

The metal salts used may be all iron or manganese salts which form stable metal complexes with the ligands of the formula (1). Preference is given to using sulfates and chlorides, and particular preference to using iron(II) chloride, iron(II) sulfate, manganese(II) chloride or manganese(II) sulfate. In an especially preferred embodiment of the invention, these metal salts are used as metal salt hydrates. Among these, preference is given in turn to the tetrahydrates Fe(II)Cl₂.4H₂O and Mn(II)Cl₂.4H₂O.

The process according to the invention optionally takes place in the presence of water, and preferably takes place in the presence of water when metal complexes of the formula (2) in which z is defined as $C(OH)_2$ are prepared. Preference is given to introducing the water into the process according to the invention by use of metal salt hydrates, more preferably in the form of $Fe(II)Cl_2.4H_2O$ or $Mn(II)Cl_2.4H_2O$. The metal salt can optionally also be introduced in the form of a concentrated aqueous solution or of a slurry of the metal salt. Preference is given here to 20 to 80% by weight solutions or slurries, in order to minimize the water content in the end product.

The ligands of the formula (1) used in the process according to the invention are complexed by the process and are thus found in the metal complexes of the formula (2) prepared. However, they can be modified in the metal complexes of the formula (2) in such a way that a ketone or carbonyl group z (z=C=O) present in the starting ligands of the formula (1) is converted to the hydrated form by any water present during the process according to the invention (z=$C(OH)_2$). This means that, in the presence of water, the ligands in the metal complexes of the formula (2) may be present as dihydroxy ketals even if they have been used in the form of ketones in the process according to the invention.

In order to obtain the particularly preferred complexes of the formula (2) in which the keto group (z is C=O) is in hydrate form (z is $C(OH)_2$), it is preferable in turn that at least 1 molecule of water is present per 1 molecule of ligand of the formula (1) in the reaction mixture. This is especially true when the ligands of the formula (1) used in the process according to the invention are those in which z is C=O.

Since the ligands of the formula (1) are virtually insoluble in water, the amount of water present during the reaction has no influence on the reaction rate, provided that at least 1 mol of water is present per 1 mol of ligand, especially in the case that complexes of the formula (2) in which z is $C(OH)_2$ are prepared from ligands of the formula (1) in which z is C=O used in the process.

Presence of the ligands in complexed form as dihydroxy ketals (z=$C(OH)_2$) can be shown, for example, by x-ray structure analysis (see, for example, Inorg. Chimica Acta, 337 (2002) 407-419).

In a particularly preferred embodiment of the process according to the invention, a homogeneous solution comprising one or more complexes of the formula [MnLCl]Cl or [FeLCl]Cl in 1,2-propylene glycol is prepared, where L is dimethyl 2,4-di(2-pyridyl)-3-methyl-7-(pyridin-2-ylmethyl)-3,7-diazabicyclo[3.3.1]nonan-9-one-1,5-dicarboxylate (N2Py3o), dimethyl 2,4-di(2-pyridyl)-3,7-dimethyl-3,7-diazabicyclo[3.3.1]nonan-9-one-1,5-dicarboxylate (N2Py2), or the corresponding dihydroxy ketals (z=$C(OH)_2$). This involves reacting dimethyl 2,4-di(2-pyridyl)-3-methyl-7-(pyridin-2-ylmethyl)-3,7-diazabicyclo[3.3.1]nonan-9-one-1,5-dicarboxylate, dimethyl 2,4-di(2-pyridyl)-3,7-dimethyl-3,7-diazabicyclo[3.3.1]nonan-9-one-1,5-dicarboxylate or the corresponding dihydroxy ketals or mixtures of these substances with manganese(II) chloride or iron(II) chloride in 1,2-propylene glycol. The manganese(II) chloride or iron(II) chloride is preferably used in the form of the solid salts, in the form of hydrates thereof, especially of the tetrahydrates, or in the form of concentrated solutions or slurries of the solid salts or hydrates in water (preferably 20 to 80% by weight in strength) or in 1,2-propylene glycol. The process thus optionally takes place in the presence of water. In an embodiment preferred in turn in this aspect of the process according to the invention, a homogeneous solution comprising one or more complexes of the formula [MnCLI]Cl is prepared, in which L is dimethyl 2,4-di(2-pyridyl)-3,7-dimethyl-3,7-diazabicyclo[3.3.1]nonan-9-one-1,5-dicarboxylate (N2Py2) or the corresponding dihydroxy ketal, and wherein dimethyl 2,4-di(2-pyridyl)-3,7-dimethyl-3,7-diazabicyclo[3.3.1]-nonan-9-one-1,5-dicarboxylate (N2Py2) or the corresponding dihydroxy ketal or mixtures thereof are reacted with manganese(II) chloride in 1,2-propylene glycol. In a further embodiment preferred in turn in this aspect of the process according to the invention, a solution comprising one or more complexes of the formula [FeLCl]Cl is prepared, in which L is dimethyl 2,4-di(2-pyridyl)-3-methyl-7-(pyridin-2-ylmethyl)-3,7-diazabicyclo-[3.3.1]nonan-9-one-1,5-dicarboxylate (N2Py3o) or the corresponding dihydroxy ketal, and wherein dimethyl 2,4-di(2-pyridyl)-3-methyl-7-(pyridin-2-ylmethyl)-3,7-diazabicyclo[3.3.1]nonan-9-one-1,5-dicarboxylate (N2Py3o) or the corresponding dihydroxy ketal or mixtures thereof are reacted with iron(II) chloride in 1,2-propylene glycol. In a particularly preferred embodiment of the process according to the invention specified here, especially when water is to be introduced into the system, the metal salt hydrates, preferably the tetrahydrates, are used in solid form or as a solution or slurry in water, or 1,2-propylene glycol, preferably in 1,2-propylene glycol. It is also possible to use the metal salts which are not in the form of hydrates as a solution or slurry in water.

Stirring is continued until a clear, homogeneous solution has formed. Through the process according to the invention, it is thus possible to directly obtain homogeneous solutions of the metal complexes of the formula (2) in di- or polyols, monoethers thereof or mixtures of these substances. After formation of the solution, the concentration of the solution can also be diluted further by addition of further di- or polyol, monoethers thereof or mixtures of these substances.

Coordinating compounds X of the metal complexes of the formula (2) preferably originate from the iron or manganese salt used in the process according to the invention.

Noncoordinating counterions Y can preferably also originate from the iron or manganese salt used in the process according to the invention, for example when Y has the same definition as X.

In a preferred embodiment of the invention, X and Y have the same definition.

In a further preferred embodiment of the invention, X and Y have different definitions. In this case, it is possible, for example, first to prepare metal complexes of the formula (2) in which X and Y have the same definition and are more preferably chloride, and then to exchange the noncoordinating counterion Y. In this procedure, for exchange of Y, preference is given to using an alkali metal or alkaline earth metal salt containing the new noncoordinating counterion Y. For example, it is possible to obtain metal complexes of the formula (2) where Y=$PF_6^-$ (hexafluorophosphates) by first preparing metal complexes where X=Y=$Cl^-$ and then exchanging the noncoordinating $Cl^-$ counterion by means of $KPF_6$ for the new noncoordinating $PF_6^-$ counterion. Such exchange reactions are common knowledge to the person skilled in the art.

In a further preferred embodiment of the process according to the invention, the ligands L are used in the process in the form of the ketones (z=C=O).

In a further preferred embodiment of the process according to the invention, a solution comprising one or more metal complexes of the formula (2) is prepared, in which the complexed ligands L are in the form of the dihydroxy ketals (z=$C(OH)_2$).

Examples which follow are intended to illustrate the invention in detail, without restricting it thereto.

EXAMPLE 1

Preparation of the dimethyl 2,4-di(2-pyridyl)-3-methyl-7-(pyridin-2-ylmethyl)-3,7-diazabicyclo[3.3.1]nonan-9-one-1,5-dicarboxylate (N2Py3o)

11.2 kg of dimethyl acetonedicarboxylate (purity 97% by weight; 64 mol) are dissolved in 15 kg of isobutanol. The solution is cooled to 10° C., then 13.4 kg of pyridin-2-aldehyde (purity 99% by weight, 125 mol) in 10 kg of isobutanol, followed by 4.8 kg of methylamine (40% by weight in water, 62 mol) are added dropwise such that the temperature is maintained with constant cooling. The reaction mixture is then heated to 40-45° C. and an azeotrope (17 liters) of isobutanol and water is distilled off under reduced pressure at internal temperature 40-45° C. During this, 15 liters of isobutanol are metered in continuously. After cooling to room temperature, 8.4 kg of aminomethylpyridine (78 mol) are metered in and the metering funnel is rinsed with 7.0 kg of isobutanol. Then 13.5 kg of formaldehyde solution (37% by weight in water, 166.5 mol) are added within 15-30 minutes. After addition has ended, the mixture is heated to 55-60° C. and stirred for a further 1.5 hours. Subsequently, at maximum internal temperature 60° C., 55 kg of azeotropic mixture of isobutanol and water are distilled off, while 36 kg of isobutanol are added continuously. The mixture is vented with nitrogen and cooled to room temperature. The precipitate formed is filtered off and washed with isobutanol. The ligand can be used in the complexation reaction in the form of the moist filtercake, or else dried under reduced pressure at 50° C. This affords 23.3 kg (72.1%) of dimethyl 2,4-di(pyridyl)-3-methyl-7-(pyridin-2-ylmethyl)-3,7-diazabicyclo[3.3.1]nonan-9-one-1,5-dicarboxylate in the form of a colorless, crystalline powder.

EXAMPLE 2

The dimethyl 2,4-di(2-pyridyl)-3,7-dimethyl-3,7-diazabicyclo[3.3.1]nonan-9-one-1,5-dicarboxylate ligand was prepared analogously to the literature: R. Haller, Arch. Pharm., 1968, 301, 741ff. and R. Haller, Arch. Pharm., 1968, 302, 113ff.

EXAMPLE 3

4.39 g (0.01 mol) of dimethyl 2,4-di(2-pyridyl)-3,7-dimethyl-3,7-diazabicyclo[3.3.1]nonan-9-one-1,5-dicarboxylate (prepared according to example 2) are suspended at room temperature in 576.5 g of 1,2-propylene glycol. Subsequently, 1.98 g (0.01 mol) of Mn(II)Cl$_2$ tetrahydrate are added and the heterogeneous mixture is stirred for 5 hours, which gives rise to a homogeneous beige solution. This gives a 1% by weight solution of the manganese complex [MnLCl]Cl (L=dimethyl 2,4-di(2-pyridyl)-3,7-dimethyl-3,7-diazabicyclo[3.3.1]nonan-9-one-1,5-dicarboxylate), where the ketone may be present in the form of the hydrate.

In examples 4-7 which follow, the notation "N2Py3o dihydroxy ketal" means that the keto group of the ligand in the metal complex is present as the hydrate or dihydroxy ketal.

EXAMPLE 4

77.7 g (0.15 mol) of coarse N2Py3o crystals (prepared analogously to example 1) are suspended in 350.8 g of 1,2-propylene glycol. 29.7 g of iron(II) chloride tetrahydrate in the form of a 30% by weight solution in 1,2-propylene glycol are added dropwise at room temperature while stirring within 2 hours, in the course of which a slightly exothermic reaction occurs. Within a continued stirring time of 5 hours at room temperature, a homogeneous yellow solution of [Fe(N2Py3o dihydroxy ketal)Cl]Cl in 1,2-propylene glycol is obtained. According to HPLC analysis, a 19.7% by weight solution of [Fe(N2Py3o dihydroxy ketal)Cl]Cl in 1,2-propylene glycol is obtained, but is found to be metastable in this concentration and, in the course of prolonged standing, gives rise to a suspension unless it is diluted to a concentration of ≤8% by weight by the further addition of 1,2-propylene glycol. Free N2Py3o ligand is analytically undetectable in the reaction mixture. Analytical studies show that the keto group of the ligand in the metal complex is present as the hydrate or dihydroxy ketal and not as the cyclic ketal of 1,2-propanediol.

EXAMPLE 5

77.7 g (0.15 mol) of coarse N2Py3o crystals (prepared analogously to example 1) are suspended in 394 g of 1,2-propylene glycol. 31.6 g (0.157 mol) of solid iron(II) chloride tetrahydrate is added in one portion at room temperature while stirring, in the course of which a slightly exothermic reaction occurs. Within a continued stirring time of 3 hours at 50° C., a homogeneous yellow solution of [Fe(N2Py3o-dihydroxy ketal)Cl]Cl in 1,2-propylene glycol is obtained. According to HPLC analysis, a 20.9% by weight solution of [Fe(N2Py3o-dihydroxy ketal)Cl]Cl in 1,2-propylene glycol is obtained. Free N2Py3o ligand is undetectable in the reaction solution. The solution is metastable and is converted over a long period to a suspension unless it is diluted to a concentration of ≤8% by weight of [Fe(N2Py3o-dihydroxy ketal)Cl]Cl.

EXAMPLE 6

77.7 g (0.15 mol) of coarse N2Py3o crystals (prepared analogously to example 1) are suspended in 350.8 g of 1,2-propylene glycol. 64.0 g of a 30% by weight solution of iron(II) chloride in water (0.152 mol of iron(II) chloride) are added at room temperature while stirring within 2 hours, in the course of which a slightly exothermic reaction occurs. Within a continued stirring time of 3 hours at 20° C., a homogenous yellow solution of [Fe(N2Py3o-dihydroxy ketal)Cl]Cl in 1,2-propylene glycol is obtained, which is adjusted by addition of further 1,2-propylene glycol to a concentration of 1% by weight of [Fe(N2Py3o-dihydroxy ketal)Cl]Cl in 1,2-propylene glycol. Free N2Py3o ligand is analytically undetectable in the reaction solution.

EXAMPLE 7

3.9 g (0.0075 mol) of coarse N2Py3o crystals (prepared analogously to example 1) are suspended in 488 g of 1,2-propylene glycol. 5.0 g of a 30% by weight solution of iron(II) chloride tetrahydrate in water or 1,2-propylene glycol (0.0075 mol of iron(II) chloride tetrahydrate) are added at room temperature while stirring within 2 hours. Within a continued stirring time of 3 hours at 20° C., a homogenous, yellow, 1% by weight [Fe(N2Py3o-dihydroxy ketal)Cl]Cl solution in 1,2-propylene glycol is obtained. Free ligand is no longer detectable by means of HPLC.

The invention claimed is:
1. A process for preparing a homogeneous solution comprising at least one metal complex of formula (2)

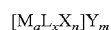

$$[M_a L_x X_n] Y_m \qquad (2)$$

where

M is a metal selected from the group consisting of Mn(II), Mn(III), Mn(IV), Fe(II), Fe(III) and Fe(IV), X is a coordinating compound selected from the group consisting of singly, doubly and triply charged anions or uncharged molecules capable of mono-, bi- or tridentate coordination to a metal, Y is a noncoordinating counterion which ensures the charge balance of the complex, a is a number from 1 to 2, x is a number from 1 to 2, n is a number from 0 to 4, m is a number from 0 to 8, and L is a ligand of formula (1) or the protonated or deprotonated form thereof

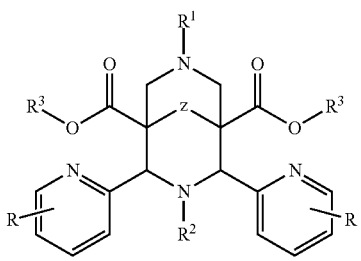

(1)

where

R is hydrogen, hydroxyl or $C_1$-$C_4$ alkyl;

$R^1$ is $C_1$-$C_4$ alkyl, $C_6$-$C_{10}$ aryl, pyridinyl-$C_1$-$C_4$-alkyl or $(CH_2)_kN(C_1$-$C_4alkyl)_2$;

$R^2$ is $C_1$-$C_{20}$ alkyl, $C_6$-$C_{10}$ aryl or pyridinyl-$C_1$-$C_4$-alkyl;

$R^3$ is $C_1$-$C_4$ alkyl;

z is C=O or $C(OH)_2$ and k is a number from 1 to 6, in di- or polyols, monoethers thereof or mixtures of these substances, which comprises the step of reacting at least one ligand of the formula (1) with an iron or manganese salt in heterogeneous reaction in the di- or polyol, the monoethers or mixtures of these substances to produce the homogeneous solution comprising at least one metal complex of formula (2).

2. The process as claimed in claim 1, wherein X is selected from the group consisting of $OH^-$, $NO_3^-$, NO, $S^{2-}$, $R^aS^-$, $PO_4^{3-}$, $H_2O$, $CO_3^{2-}$, $R^bOH$, $Cl^-$, $Br^-$, $CN^-$, $ClO_4^-$, $R^aCOO^-$ and $SO_4^{2-}$, where $R^a$ is H or $C_1$-$C_4$ alkyl and $R^b$ is $C_1$-$C_4$ alkyl.

3. The process as claimed in claim 1, wherein Y is selected from the group consisting of $R^cSO_4^-$, $SO_4^{2-}$, $NO_3^-$, $Cl^-$, Br, $I^-$, $ClO_4^-$, $BF_4^-$, $PF_6^-$ and $R^cSO_3^-$, where $R^c$ is H or $C_1$-$C_4$ alkyl.

4. The process as claimed in claim 1, wherein the solutions comprising at least one complex of the formula [FeLCl]Cl, [FeL($SO_4$)], [MnLCl]Cl or [MnL($SO_4$)] are prepared, where L is selected from the group consisting of dimethyl 2,4-di(2-pyridyl)-3-methyl-7-(pyridin-2-ylmethyl)-3,7-diazabicyclo[3.3.1]nonan-9-one-1,5-dicarboxylate (N2Py3o), dimethyl 2,4-di(2-pyridyl)3-(pyridin-2-ylmethyl)-7-methyl-3,7-diaza-bicyclo[3.3.1]nonan-9-one-1,5-dicarboxylate (N2Py3u), diethyl 2,4-di(2-pyridyl)-3-methyl-7-(pyridin-2-ylmethyl)-3,7-diazabicyclo[3.3.1]nonan-9-one-1,5-dicarboxylate, dimethyl 2,4-di(2-pyridyl)-3,7-bis(pyridin-2-ylmethyl)-3,7-diazabicyclo[3.3.1]nonan-9-one-1,5-dicarboxylate (N2Py4), dimethyl 2,4-di(2-pyridyl)-3,7-dimethyl-3,7-diazabicyclo[3.3.1]nonan-9-one-1,5-dicarboxylate (N2Py2), diethyl 2,4-di(2-pyridyl)-3,7-dimethyl-3,7-diazabicyclo[3.3.1]nonan-9-one-1,5-dicarboxylate, dimethyl 2,4-di(2-pyridyl)-3-methyl-7-(N,N'-dimethylethylamine)-3,7-diazabicyclo[3.3.1]nonan-9-one-1,5-dicarboxylate and the corresponding dihydroxy ketals.

5. The process as claimed in claim 1, wherein the di- or polyols have 2 to 6 carbon atoms and 2 to 4 OH groups and the monoethers of these di- and polyols contain alcohol units originating from monoalcohols having 1 to 4 carbon atoms.

6. The process as claimed in claim 1, wherein the process is conducted in the di- or polyols or mixtures thereof.

7. The process as claimed in claim 5, wherein the process is conducted in 1,2-propylene glycol.

8. The process as claimed in claim 1, wherein the solution prepared contains 0.01 to 30% by weight of complex of the formula (2).

9. The process as claimed in claim 1, wherein the complexation reaction is performed within the temperature range from 5 to 80° C.

10. The process as claimed in claim 1, wherein the ligands of the formula (1) are selected from the group consisting of dimethyl 2,4-di(2-pyridyl)-3-methyl-7-(pyridin-2-ylmethyl)-3,7-diazabicyclo[3.3.1]nonan-9-one-1,5-dicarboxylate (N2Py3o), dimethyl 2,4-di(2-pyridyl)-3,7-dimethyl-3,7-diazabicyclo[3.3.1]nonan-9-one-1,5-dicarboxylate (N2Py2) and the corresponding dihydroxy ketals.

11. The process as claimed in claim 1, wherein the complexation reaction is performed by first introducing the ligand of the formula (1) into the di- or polyol, monoethers thereof or mixtures of these substances to prepare a suspension containing 0.5 to 60% by weight of ligand and then adding the metal salt in solid or dissolved form within the temperature range from 5 to 80° C.

12. The process as claimed in claim 1, wherein the iron or manganese salt used is iron(II) chloride, iron(II) sulfate, manganese(II) chloride or manganese(II) sulfate.

13. The process as claimed in claim 1, wherein z is $C(OH)_2$ and the metal salts are metal salt hydrates.

14. The process as claimed in claim 13, wherein the iron or manganese salt hydrates are selected from the group consisting of Fe(II)$Cl_2$·$4H_2O$ and Mn(II)$Cl_2$·$4H_2O$.

15. The process as claimed in claim 1, wherein the solution comprising at least one complex of the formula [MnLCl]Cl or [FeLCl]Cl in 1,2-propylene glycol is prepared, where L is dimethyl 2,4-di(2-pyridyl)-3-methyl-7-(pyridin-2-ylmethyl)-3,7-diazabicyclo[3.3.1]nonan-9-one-1,5-dicarboxylate (N2Py3o), dimethyl 2,4-di(2-pyridyl)-3,7-dimethyl-3,7-diazabicyclo[3.3.1]nonan-9-one-1,5-dicarboxylate (N2Py2), or the corresponding dihydroxy ketals (z=$C(OH)_2$), and dimethyl 2,4-di(2-pyridyl)-3-methyl-7-(pyridin-2-ylmethyl)-3,7-diazabicyclo[3.3.1]nonan-9-one-1,5-dicarboxylate, 2,4-di(2-pyridyl)-3,7-dimethyl-3,7-diazabicyclo[3.3.1]nonan-9-one-1,5-dicarboxylate or the corresponding dihydroxy ketals or mixtures of these substances are reacted with manganese (II) chloride or iron(II) chloride in 1,2-propylene glycol.

16. The process as claimed in claim 1, wherein the at least one ligand L is in the form of a ketone.

17. The process as claimed in claim 1, wherein the solution prepared contains 0.1 to 15% by weight of complex of the formula (2).

18. The process as claimed in claim 1, wherein the solution prepared contains 0.5 to 8% by weight of complex of the formula (2).

19. The process as claimed in claim 1, wherein the complexation reaction is performed within the temperature range from 10 to 70° C.

20. The process as claimed in claim 1, wherein the complexation reaction is performed within the temperature range from 15 to 55° C.

* * * * *